United States Patent [19]

Nelson et al.

[11] Patent Number: 5,991,697
[45] Date of Patent: Nov. 23, 1999

[54] METHOD AND APPARATUS FOR OPTICAL DOPPLER TOMOGRAPHIC IMAGING OF FLUID FLOW VELOCITY IN HIGHLY SCATTERING MEDIA

[75] Inventors: John Stuart Nelson, Laguna Niguel; Thomas Edward Milner; Zhongping Chen, both of Irvine, all of Calif.

[73] Assignee: The Regents of the University of California, Oakland, Calif.

[21] Appl. No.: 08/775,279

[22] Filed: Dec. 31, 1996

[51] Int. Cl.⁶ ........................................... G01P 3/36
[52] U.S. Cl. ...................... 702/49; 702/45; 702/76; 382/107; 382/131; 356/28.5; 600/425; 600/441; 600/453
[58] Field of Search ................... 702/49, 19, 21, 702/22, 28, 30, 32, 40, 45, 50, 75, 76, 87, 88, 100, 159, 189; 365/528.17; 382/107, 128, 131, 133, 134; 600/425, 427, 441, 453–457; 73/861.25, 861, 861.02, 861.03, 863, 863.01–863.03, 601–603, 605, 606, 618; 367/7, 10; 356/337, 345, 346, 348, 349, 351, 352, 359–361, 39, 40, 301, 73.1, 27, 28, 28.5; 250/363.04, 550; 324/304–306, 310, 312

[56] References Cited

U.S. PATENT DOCUMENTS

| 5,501,226 | 3/1996 | Petersen et al. | 356/28.5 |
| 5,551,434 | 9/1996 | Iinuma | 600/455 |
| 5,587,785 | 12/1996 | Kato et al. | 356/28.5 |

OTHER PUBLICATIONS

Bail et al, "Optical Coherence Tomography With the 'Spectral Radar' Fast Optical Analysis in Volume Scatters By Short Coherence Interferometry" (No Date).
Chen et al., "Optical Doppler tomography: Imaging in vivo Blood Flow Dynamics Following Pharmacological Intervention and Photodynamic Therapy" (1997) pp. 1–20 (Jul. 1997).
Gusmeroli et al., "Distributed laser Doppler velocimeter" (1991) Optics Letters vol. 16 No. 17 pp. 1358–1360 (Jun. 1991).
Barton et al., "Optical Low–Coherence Reflectometry to Enhance Monte Carlo Modeling of Skin" (1997) Journal of Biomedical Optics vol. 2 No. 2 pp. 226–234 (Apr. 1997).
Huang et al., "Optical Coherence Tomography" (1991) Science, vol. 254, pp. 1178–1181 (Nov. 1991).
Chen et al., "Optical Doppler tomographic imaging of fluid flow velocity in highly scattering media" (1997) Optics Letters, vol. 22, No. 1, pp. 64–66 (Jan. 1997).
Chen, et al., "Noninvasive imaging of in vivo blood flow velocity using optical Doppler tomography" (1997) Optics Letters, vol. 22, No. 14, pp. 1119–1121, (Jul. 1997).
Wang et al., "Characterization of fluid flow velocity by optical Doppler tomography" (1995) Optics Letters, vol. 20, No. 11, pp. 1337–1339, (Jun. 1995).

Primary Examiner—Hal Dodge Wachsman
Attorney, Agent, or Firm—Daniel L. Dawes

[57] ABSTRACT

Optical Doppler tomography permits imaging of fluid flow velocity in highly scattering media. The tomography system combines Doppler velocimetry with high spatial resolution of partially coherent optical interferometry to measure fluid flow velocity at discrete spatial locations. Noninvasive in vivo imaging of blood flow dynamics and tissue structures with high spatial resolutions of the order of 2 to 10 microns is achieved in biological systems. The backscattered interference signals derived from the interferometer may be analyzed either through power spectrum determination to obtain the position and velocity of each particle in the fluid flow sample at each pixel, or the interference spectral density may be analyzed at each frequency in the spectrum to obtain the positions and velocities of the particles in a cross-section to which the interference spectral density corresponds. The realized resolutions of optical Doppler tomography allows noninvasive in vivo imaging of both blood microcirculation and tissue structure surrounding the vessel which has significance for biomedical research and clinical applications.

22 Claims, 9 Drawing Sheets

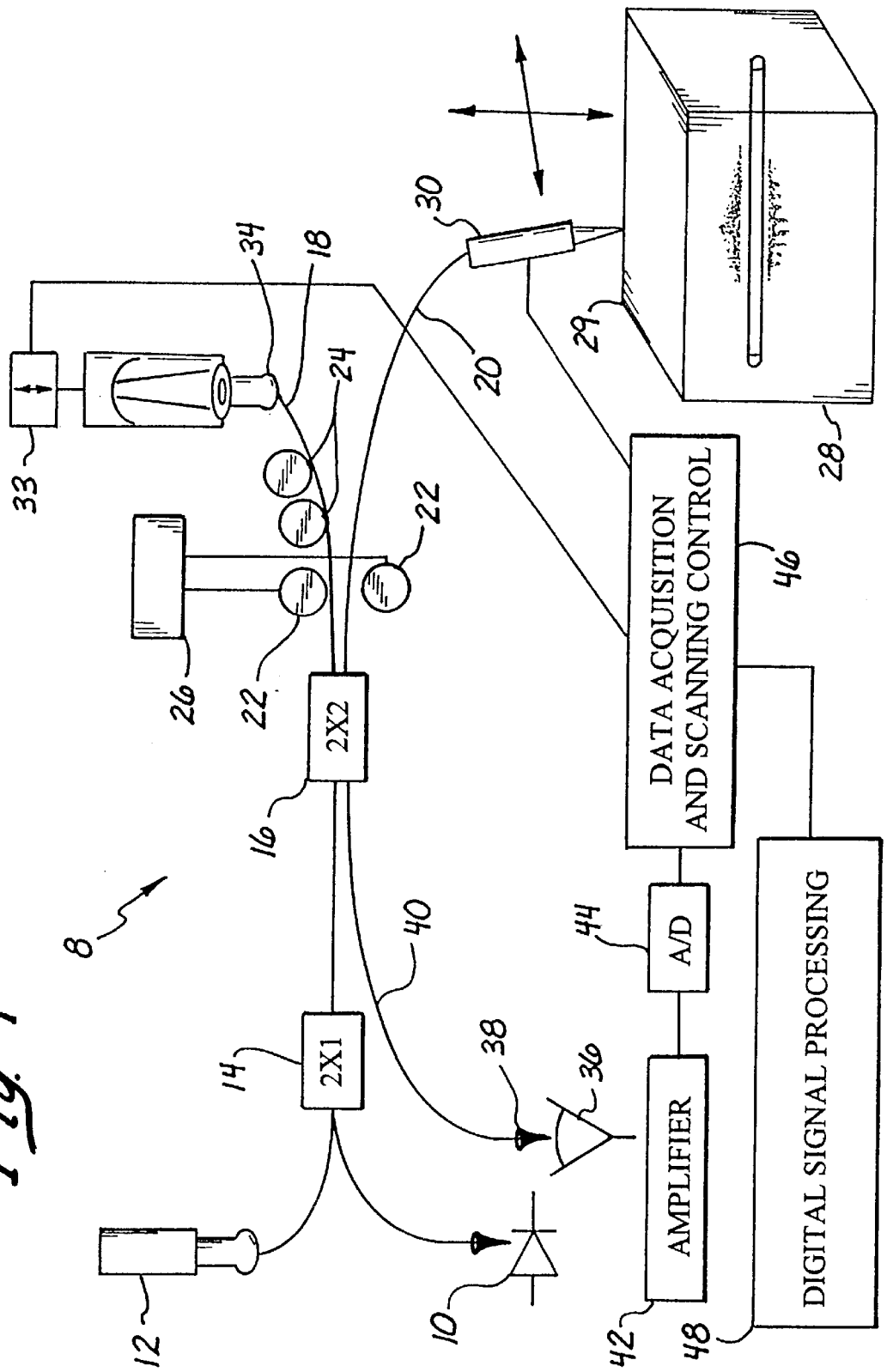

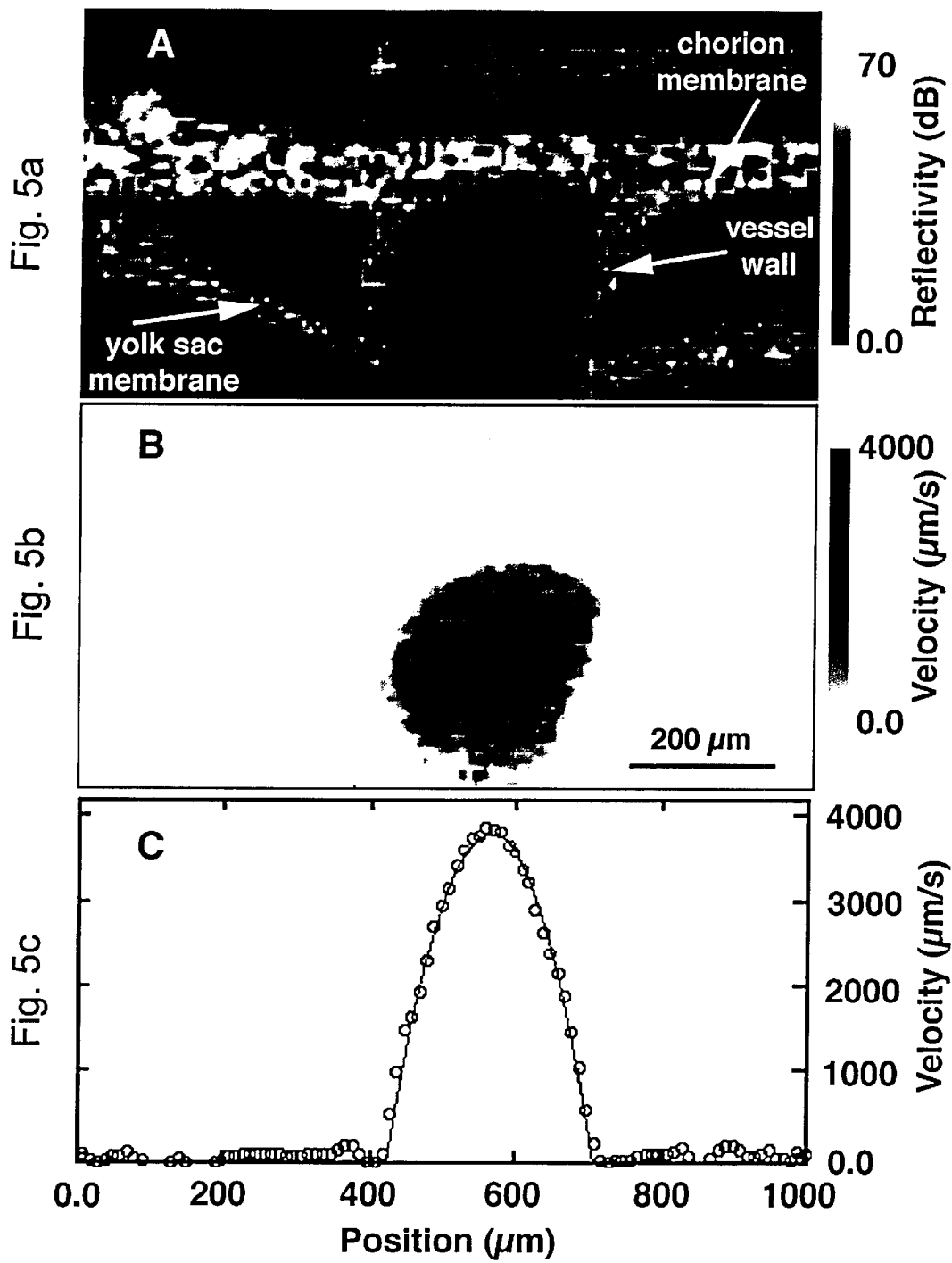

Fig. 6a
Fig. 6a'
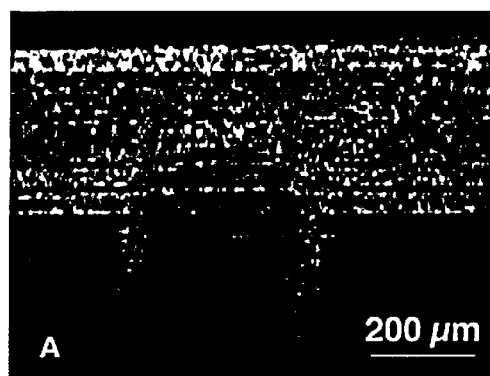
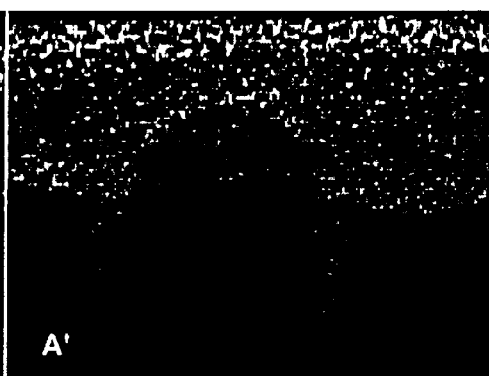
Fig. 6b
Fig. 6b'

Fig. 7a
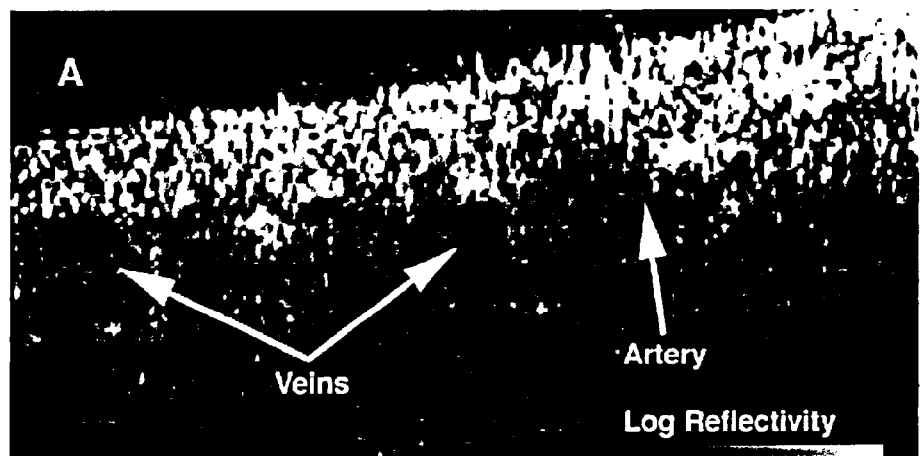
Fig. 7b
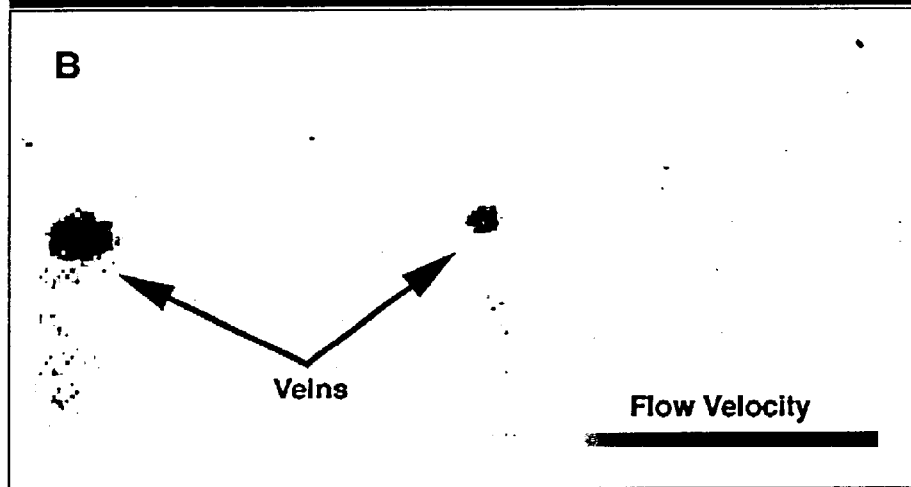
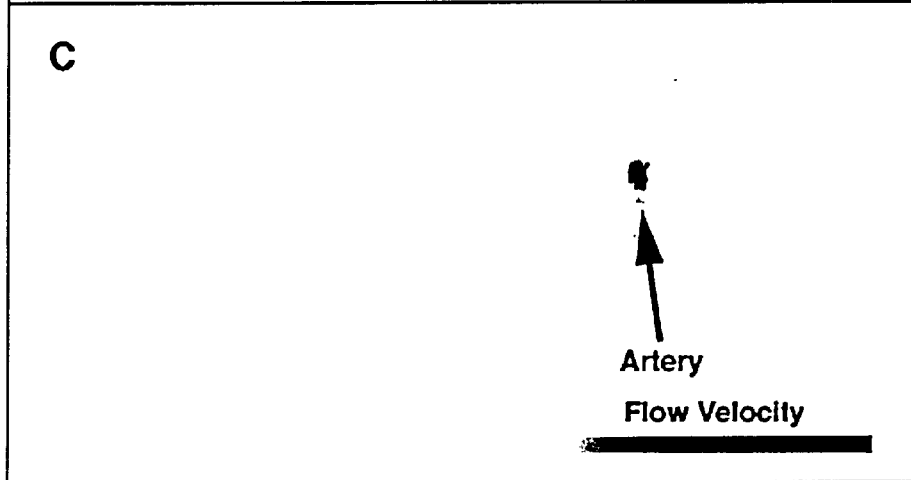
Fig. 7c

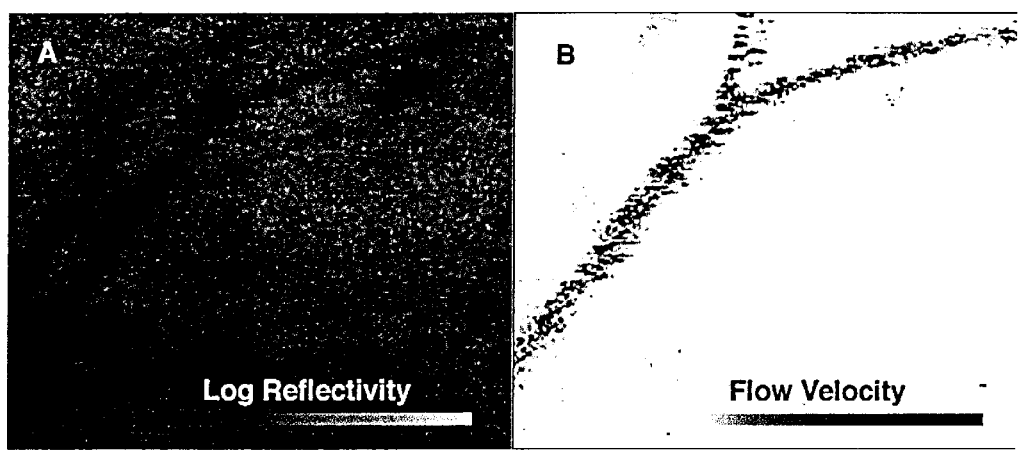
Fig. 8a                    Fig. 8b

METHOD AND APPARATUS FOR OPTICAL DOPPLER TOMOGRAPHIC IMAGING OF FLUID FLOW VELOCITY IN HIGHLY SCATTERING MEDIA

The government may have rights to the invention under National Institute of Health contracts 1R29AR41638-01A1; 1R01AR42437-01A1; and 1R03RR6988-01.

BACKGROUND OF THE INVENTION

1. Field of the Invention

The invention relates to the field of noninvasive tomography and in particular is applied to tomographic methods and apparatus for simultaneous optical detection of blood flow velocity and vessel structure. Noninvasive in vivo imaging of blood flow dynamics and tissue structures with high spatial resolutions of the range of 2 to 10 microns is achieved in biological systems.

2. Description of the Prior Art

Accurate determination of location and flow velocity of moving particles in highly scattering media, such as biological tissues, is important for medical diagnostics. Development of a high resolution noninvasive technique for in vivo blood flow imaging with a resolution in the range of 2 to 10 microns is necessary for accurate microvascular monitoring. The ideal microvascular imaging technique must fulfill several requirements: (a) probe the underlying microcirculation at a user-specified depth in both superficial and deep layers; (b) distinguish arterial from venous flow; (c) detect blood flow changes rapidly; and (d) be safe, noninvasive, reliable and reproducible. Numerous approaches have been investigated including Doppler ultrasound, conventional angiography, laser Doppler flowmetry and magnetic resonance angiography. Each of these techniques however have their limitations. Conventional laser Doppler flowmetry, for example, has been used to measure mean blood perfusion in the peripheral microcirculation. However, because of strong optical scattering in biological tissue, laser Doppler flowmetry cannot identify blood flow velocity at discrete spatial locations with micron resolution. Although Doppler ultrasound imaging provides a means to resolve flow velocities at different locations in the scattering medium, the relatively long acoustic wavelength required for deep tissue penetration limits spatial resolution to approximately 200 microns.

Therefore, what is needed is a method and apparatus that may be used in vivo to determine flow velocities in a turbid or highly scattering medium such as biological tissues with spatial and velocity resolutions equal or greater than those obtained by other methods.

BRIEF SUMMARY OF THE INVENTION

The invention is a method for tomographic imaging of a fluid flow in a highly scattering medium comprising the steps of scanning a fluid flow sample with an optical source of at least partially coherent radiation through an interferometer. The radiation in the interferometer is phase modulated at a modulation frequency. Equivalently, the phase modulation can be defined as modulating the optical path length in the interferometer. Where the claims call for "phase modulation", it should be read to include modulation of the optical path length. The interference fringes formed by radiation backscattered from the sample and reflected from the reference mirror are detected. The Doppler frequency changes of the detected backscattered interference fringes with respect to the modulation frequency are detected at each pixel of a scanned image to form a tomographic image of the scanned fluid flow sample. As a result, tomographic images of fluid flow sample structure and velocity are noninvasively obtained.

The fluid flow sample is scanned with an optical source of at least partially coherent radiation through a fiberoptic Michelson interferometer. The interferometer has a reference beam and a sample beam and the step of scanning the fluid flow sample with the source of radiation through the interferometer further comprises the step of matching the polarity of the reference and the sample beams to optimize fringe contrast and equalize optical pathlengths in the interferometer. The reference beam is attenuated to reduce photon bunching and noise and increase signal-to-noise ratio of interference fringes formed between light backscattered from the sample and reflected from the reference mirror within the interferometer.

The step of scanning the fluid flow sample with the source of radiation through the interferometer further comprises phase modulating the radiation provided by the source. The step of scanning the fluid flow sample with modulated radiation comprises modulating the optical path lengths of the radiation in either of the reference and sample beams of the interferometer.

The interferometer has a reference mirror disposed in the reference optical path. The radiation has a beam waist in the sample path or more properly in the sample itself. The method further comprises the step of dynamically maintaining a zero optical path length difference between light backscattered from the beam waist in the sample and the reference mirror notwithstanding axial movement of the beam waist in the fluid flow sample by means of providing a compensating axial movement of the reference mirror in the reference optical path as the sample is scanned. The scanning step includes making a plurality of incremental axial scanning movements to maintain a zero optical path length difference between the beam waist in the sample and the reference mirror. The step of maintaining the zero optical path length difference comprises compensating for each incremental axial scanning movement with a corresponding axial movement in the reference mirror to maintain a zero optical path length difference between the beam waist in the sample and the reference mirror as the sample is scanned.

The step of detecting backscattered interference fringes comprises the step of measuring optical interference fringe intensity, digitizing the measured optical interference fringe intensity at each pixel of an image, and computing the power spectrum of the interference fringe intensity at each pixel of the image to obtain a frequency spectrum at each pixel. The method further comprises calculating the power of the frequency component corresponding to the phase modulation from the power spectrum at each pixel to generate a tomographic structural image of the fluid flow sample. The method also comprises the step of generating a tomographic image of fluid flow velocity at each pixel by measurement of Doppler shifted frequency at each pixel with respect to the phase modulation frequency. In particular, the tomographic fluid flow image is generated by calculating the Doppler shifted frequency from a difference between the centroid of the power spectrum at each pixel and the phase modulation frequency.

The invention is also an apparatus for performing optical Doppler tomographic imaging of fluid flow velocity in a highly scattering medium comprising a source of at least partially coherent radiation, and an interferometer coupled to the source of radiation. The interferometer has a reference arm for a reference beam and a sample arm for a sample beam. A scanner is coupled to the interferometer for scanning a fluid flow sample with the sample beam of the interferometer. A sensor is coupled to the interferometer for detecting backscattered radiation received by the interferometer from the scanner to detect interference fringes within the interferometer. A data processor is coupled to the sensor for processing signals from the sensor corresponding to the interference fringes established between light backscattered from the beam waist in the sample and reflected from the reference mirror in the interferometer and for controlling the scanner to generate tomographic images.

The apparatus further comprises an aiming source of light, such as a CW laser, coupled to the interferometer so that a light beam is delivered by the scanner to the fluid flow sample for purposes of aiming the scanner using the unaided human eye with respect to the fluid flow sample.

The apparatus further comprises a modulator coupled to the interferometer for modulating the optical path length difference between the reference and sample arms of the interferometer at a predetermined phase modulation frequency.

The apparatus further comprises a polarization element coupled to the interferometer to match polarity of the reference and sample beams to optimize fringe contrast and equalize optical path lengths.

The reference arm of the interferometer includes a reference mirror, and the sample beam has a beam waist. The apparatus further comprises means for maintaining a zero optical path length difference between light backscattered from the beam waist in the sample beam and the reference mirror as the beam waist is axially moved in the sample by compensating axial movement of the reference mirror.

The data processor generates a power spectrum of the interference fringe intensity at each pixel within the scan. The data processor simultaneously generates a tomographic structural image and a tomographic flow velocity image from the power spectrum at each pixel in the image.

In another embodiment the invention is defined, as above, as a method for tomographic imaging of a fluid flow in a highly scattering medium comprising the steps of: scanning a fluid flow sample with a source of at least partially coherent radiation through an interferometer to generate backscattered radiation in the interferometer; and phase modulating the radiation in the interferometer at a modulation frequency to generate a modulation of an interference spectral density of backscattered and reference radiation in the interferometer. However, in this embodiment frequencies and phase change rates of the modulation of the interference spectral density of the backscattered radiation in the interferometer are measured. A tomographic image of the scanned fluid flow sample is generated from the spectral modulation frequencies and phase change rates to simultaneously obtain positions and velocities of objects moving within the fluid flow sample. The frequencies and phase change rates of the modulation of the interference spectral density of the radiation in the interferometer are obtained by measuring the frequencies and phase change rates using an optical spectrum analyzer coupled to the interferometer to receive the interference spectral density of the backscattered radiation.

The tomographic image of the scanned fluid flow sample is generated from the spectral modulation frequencies and phase change rates of the interference spectral density to simultaneously obtain positions and velocities of objects moving within the fluid flow sample. The position of each object, $O_i$, in the fluid flow sample is obtained by measurement of the corresponding spectral period $\Gamma_i = c/2\Delta_i$ of a spectral modulation frequency, where c is the speed of light, and $\Delta_i$ is the optical path length difference between the $O_i$ object and reference mirror at t=0, where t is the time of measurement, and by measurement of a corresponding rate of phase change, $d\Phi_i/dt = 4\pi \nu V_i/c$, of the modulation frequency with spectral period $\Gamma_i$ in the interference spectral density, and where $V_i$ is the velocity of the $O_i$ object at t=0, and $\nu$ is the optical frequency.

Similarly, the invention in this alternative embodiment is also defined as an apparatus for optical Doppler tomographic imaging of fluid flow velocity in highly scattering medium comprising, as before, a source of at least partially coherent radiation; an interferometer coupled to the source of radiation, the interferometer having a reference arm for a reference beam and a sample arm for a sample beam, a modulator coupled to the interferometer for modulating optical path lengths in the reference and sample arms of the interferometer at a predetermined phase modulation frequency, and a probe coupled to the interferometer for exposing a fluid flow sample with the sample beam of the interferometer.

However, in the alternative embodiment, an optical spectrum analyzer is coupled to the output of the interferometer for detecting backscattered radiation received by the interferometer from the probe and reference mirror to analyze modulated interference spectral densities produced by the interferometer. A data processor is then coupled to the optical spectrum analyzer for processing signals from the probe corresponding to the interference spectral densities established by the backscattered radiation from the sample and reference mirror in the interferometer to generate tomographic images.

The optical spectrum analyzer measures frequencies and phase change rates of the modulation of the interference spectral density of the radiation at the output of the interferometer. The data processor generates a tomographic image of the scanned fluid flow sample from the spectral modulation frequencies and phase change rates to simultaneously obtain positions and velocities of objects moving within the fluid flow sample from the interference spectral density by obtaining the position of each object, $O_i$, in the fluid flow sample by measurement of a spectral period $\Gamma_i = c/2\Delta_i$, of a modulation frequency in the interference spectral density, where c is the speed of light, and $\Delta_i$ is the optical path length difference between the $O_i$ object and the reference mirror at t=0, where t is the time of measurement, and by measurement of a corresponding rate of phase is change $d\Phi_i/dt = 4\pi \nu V_i/c$ of the modulation frequency with the spectral period $\Gamma_i$ in the interference spectral density, where $V_i$ is the velocity of the $O_i$ object at t=0, and $\nu$ is the optical frequency.

The invention may now be better visualized by turning to the following drawings wherein like elements are referenced by like numerals.

BRIEF DESCRIPTION OF THE DRAWINGS

FIG. 1 is a highly schematic diagram of an optical Doppler tomographic system of the invention.

FIGS. 5a, 5b and 5c are optical Doppler tomographic images of in vivo blood flow in a chick chorioallantoic membrane vein. FIG. 5a is a structural tomographic image, FIG. 5b is a flow velocity tomographic image and FIG. 5c is a graph of the velocity as a function of position from the center of the vein shown in FIGS. 5a and 5b where open circles are experimental data and the solid line is a fit to a parabolic function.

FIGS. 6a and 6b are optical Doppler tomographic structural and velocity images respectively before the pharmacological intervention of a vasodilating drug, nitroglycerin, in a chick chorioallantoic membrane artery.

FIGS. 6a' and 6b' are the corresponding structural and velocity images to FIGS. 6a' and 6b' after pharmacological intervention of a vasodilating drug, nitroglycerin, to the chick chorioallantoic membrane artery.

FIGS. 7a, 7b and 7c are optical Doppler tomographic images of in vivo blood flow in rat skin. FIG. 7a is a tomographic structural image and FIG. 7b is a tomographic velocity image of in vivo venous flow. FIG. 7c is a tomographic velocity image of in vivo arterial flow in rat skin.

FIGS. 8a and 8b are in vivo face structural and velocity tomographic images respectively of blood flow in a vessel 200 microns below the skin surface in rat skin.

Figure 2A:
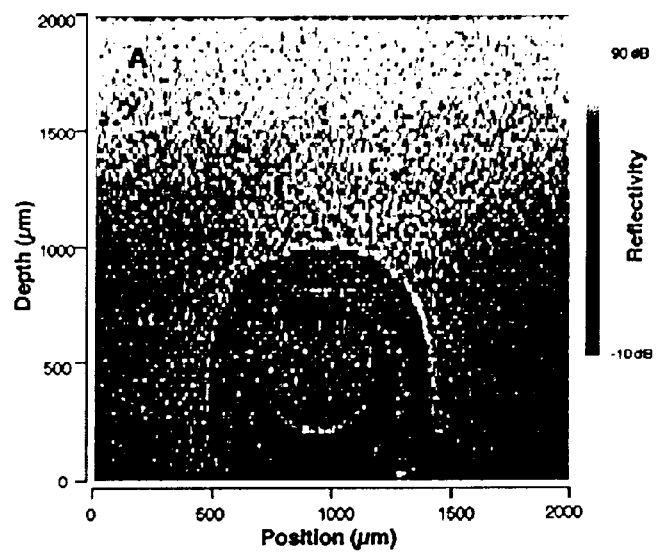
FIGS. 2a, 2b and 2c are tomographic images taken with the system of FIG. 1 of a phantom in which a circular cross-section conduit carries a flow of polystyrene beads in an intralipid suspension.

The invention and its various embodiments may now be understood in connection with the following detailed description.

DETAILED DESCRIPTION OF THE PREFERRED EMBODIMENTS

Optical Doppler tomography permits imaging of fluid flow velocity in highly scattering media. The tomography system combines Doppler velocimetry with high spatial resolution of partial coherence optical interferometry to measure fluid flow velocity at discrete spatial locations. Noninvasive in vivo imaging of blood flow dynamics and tissue structures with high spatial resolutions of the range of 2 to 10 microns is achieved in biological systems. The backscattered interference signals derived from the interferometer may be analyzed either through calculation of the interference fringe intensity power spectrum to obtain the position and velocity of each particle in the fluid flow sample at each pixel, or the interference spectral density may be analyzed at each wavelength in the optical spectrum to obtain the positions and velocities of the particles in a linear cross section through the fluid flow sample to which the spectral interference density corresponds. The realized resolutions of optical Doppler tomography allows noninvasive in vivo imaging of both blood microcirculation and tissue structure surrounding the vessel which has significance for biomedical research and clinical applications.

The optical Doppler tomography system of the invention permits imaging of the fluid flow velocity in a highly scattering media. For example, according to the invention tomographic imaging of particle flow velocity within a circular conduit submerged one millimeter below the surface in a scattering phantom of intralipid suspension is illustrated below. Second, also described below is the imaging of in vivo blood flow using optical Doppler tomography of the invention. Compared to other microvascular imaging techniques, the optical Doppler tomography of the invention is noninvasive and noncontact, has high spatial resolution within 2 to 10 microns, and provides simultaneous information regarding not only in vivo blood flow at discrete locations, but also the tissue structure surrounding the vessel. Optical Doppler tomography combines Doppler velocimetry with optical coherence tomography, as illustrated in context of the system shown in FIG. 1. Optical coherence tomography is an imaging technique that uses a Michelson interferometer with a partially coherent source, generally denoted by reference numeral 8, to form optical sections of biological materials. The amplitude of back scattered light is determined by a measurement of the interference fringe intensity generated between the reference and sample beams. High axial spatial resolution is possible because a partially coherent source is used in the interferometer.

Figure 9:
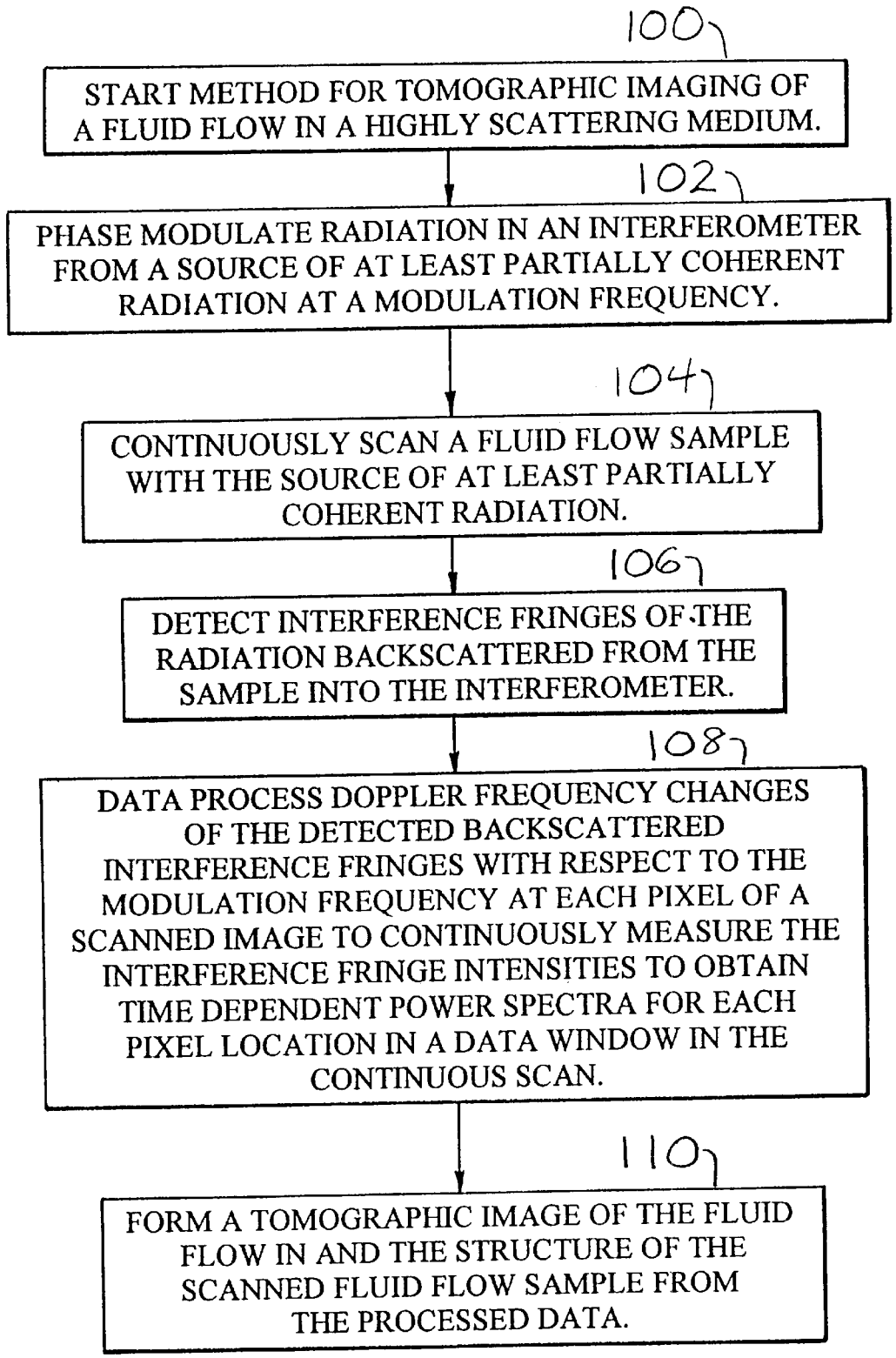
FIG. 9 is a flow chart of the methodology of the invention.

The method for tomographic imaging of a fluid flow in a highly scattering medium is diagrammatically depicted in the flow chart of FIG. 9. The method starts at step 100. The radiation from a source of at least partially coherent radiation is phase modulation in an interferometer at a modulation frequency in step 102. A fluid flow sample is continuously scanned with the source at step 104. Interference fringes of the radiation backscattered from the sample into the interferometer are then detected at step 106. The detected backscattered interference fringes are data processed at step 108 to calculate the Doppler frequency changes of with respect to the modulation frequency at each pixel of a scanned image to continuously measure the interference fringe intensities to obtain time dependent power spectra for each pixel location in a data window in the continuous scan. A tomographic image of the fluid flow in and the structure of the scanned fluid flow sample is then formed from the processed data at step 110.

Optical Doppler tomography makes use of the principle that the interference fringe frequency due to light backscattered from a moving particle and reflected from the reference mirror is Doppler shifted by $\Delta f$ according to the following formula:

$$\Delta f = \frac{1}{2\pi}(k_s - k_i)v \tag{1}$$

Where $k_i$ and $k_s$ are the wave vectors of incoming and scattered light respectively, and $v$ is the velocity vector of the moving particles. Given the angle $\theta$ between the sample beam in air and the flow direction, the Doppler shift which arises from equation 1 is simplified to the following:

$$\Delta f = 2\ v\ \cos\theta/\lambda_0 \tag{2}$$

Where $\lambda_0$ is the vacuum center wavelength of the source light. When light backscattered from a moving particle interferes with the reference beam, beating at the Doppler frequency occurs, shifting the frequency of the interference fringe intensity from that of the optical phase modulation. The sign of the frequency shift, $\Delta f$, depends on the direction of the flow velocity. The frequency shift is positive when the angle between $(k_s-k_i)$ and $v$ is less than 90°, and is negative when the angle is greater than 90°. When the angle $\theta$ is known, detection of the Doppler frequency shift, $\Delta f$, permits measurement of the particle flow velocity at discrete spatial locations.

In the optical Doppler tomographic system illustrated in FIG. 1 a superluminescent diode operating on the center frequency of 850 nm and a bandwidth of 25 nm with power at 1 mW is used as a low coherence source 10. Light from source 10 and an aiming beam generated from a helium neon laser 12, operating at a frequency of 633 nm, are coupled into fiberoptic Michelson interferometer 8 by 2×1 optic coupler 14. Light from source 10 is split into a reference and sample arm 18 and 20 respectively of interferometer 8 by a 2×2 fiber optic coupler 16. Light intensity in reference arm 18 is attenuated to 2 µW to reduce photon bunching noise and to increase the signal-to-noise ratio. Plates to provide birefringence by stress are used match the polarity of reference and sample beams in arms 18 and 20 respectively to optimize fringe contrast and equalize path length. Phase modulation is illustrated in FIG. 1 in both reference and sample arms 18 and 20, but it may be preferable in some applications to introduce phase modulations in only one of arms 18 or 20.

The optical path lengths of light in reference arm 18 and sample arm 20 are phase modulated in the illustrated embodiment at 1600 Hz with piezoelectric cylinders 24, which are electrically expanded by a ramp waveform supplied by a waveform generator 26. In the illustration sample arm 20 is tilted at about 75° with respect to the direction of fluid flow in phantom conduit 28 which is submerged in a phantom bath 29 of intralipid suspension. The angle is variable and may be controlled to effect data output as described below. Light in sample arm 20 is focused onto the sample within conduit 28 with a gradient index lens terminating the sample fiber in scanning stage 30 (N.A. 0.2). Other types of lensing could be equivalently employed to focus the sample beam.

Two-dimensional images are formed by sequential lateral scans by a conventional scanning stage lens 30 as controlled by scanning control 46 at a constant horizontal velocity of 800 microns per second followed by incremental probe movement in the vertical or axial direction. For example, total scanning time for an image size of 2000 microns×2000 microns with a pixel resolution of 10 microns×30 microns is about 8 minutes.

To maintain a zero difference in the optical path length between the beam waist in the fluid flow sample in conduit 28 and reference mirror 32 in reference arm 18 as the sample is scanned, a dynamic focus tracking method is used. Microactuators 33 are coupled to mirror 32 and to scanning control 46 for coordinated axial motion of mirror 32 with respect to axial movement of scanning lens 30. In this approach, for each incremental axial probe movement of $\delta_1$, the reference mirror is moved $\delta_2$ to compensate for the new position of the beam waist in conduit 28 in order to remove axial movement of scanning lens 30 as a source of optical path length differences between arms 18 and 20. The relationship between $\delta_1$ and $\delta_2$ as determined from geometric optics is:

$$\delta_2 = (\bar{n}^2 - 1)\delta_1$$

Where $\bar{n}$ is the mean refractive index of the fluid flow sample. Light backscattered from the sample in conduit 28 through sample arm 20 recombines with light reflected from reference mirror 32 through reference arm 18 in 2×2 coupler 16.

The optical interference fringe intensity is measured by a silicon photovoltaic receiver 36 coupled by means of fiberoptic 40 to coupler 16 and focused by lens 38 onto photoreceiver 36. Signals received by photoreceiver 36 are amplified by amplifier 42 and digitized by a 20 kHz 16-bit analog-to-digital converter 44. The output of converter 44 is transferred to a computer workstation or data acquisition and scanning control unit 46. Workstation 46 also provides scanning control for scanning lens 30, dynamic focus tracking for mirror 32, and data acquisition from photoreceiver 36.

The power spectrum of the interference fringe intensity at each pixel in the scan is determined by an algorithm within a digital signal processing section 48 of the workstation. A tomographic structural image is obtained by calculation of the power in a narrow window centered at the phase modulation frequency, i.e. 1600 kHz in this embodiment. The fluid flow velocity at each pixel location is determined by measurement of the Doppler frequency shift, which is obtained by calculation of the difference between the centroid, $f_c$, of the power spectrum at each pixel and the phase modulation frequency, $f_m$, namely $v = \Delta f \lambda_0 / 2\cos\theta = \lambda_0 (f_c - f_m)/2\cos\theta$.

The lateral and axial spatial resolution of interferometer 8 are limited by the beam spot size of approximately 5 microns and the full width half maximum spectral width of source 10 ($\Delta\lambda_{FWHM}$=25 nm). The flow velocity resolution depends on the angle between the flow velocity of the sample in conduit 28 and sample probe beam emitted from scanning stage 30 and the duration of data measurement of the interference fringe data recorded at each pixel. The experimentally determined resolution is approximately 100 microns per second and can be improved using larger angles between the sample flow velocity and the probe beam and/or longer data acquisition times.

To demonstrate particle flow velocity in the scattering medium, two phantom models are discussed below. The first model is a circular section of polyethylene conduit 28 containing a suspension of polystyrene beads of a diameter 1.7 microns with a concentration of $3.7 \times 10^5$ per mm$^3$, all of which is submerged in a phantom of 0.25% intralipid solution bath 29. The inner and outer diameters of polyethylene conduit 28 are 580 and 960 microns respectively. In a second model, the same circular conduit contains a moving suspension of 1% intralipid all submerged in a phantom of 1% intralipid solution.

Figure 2B:
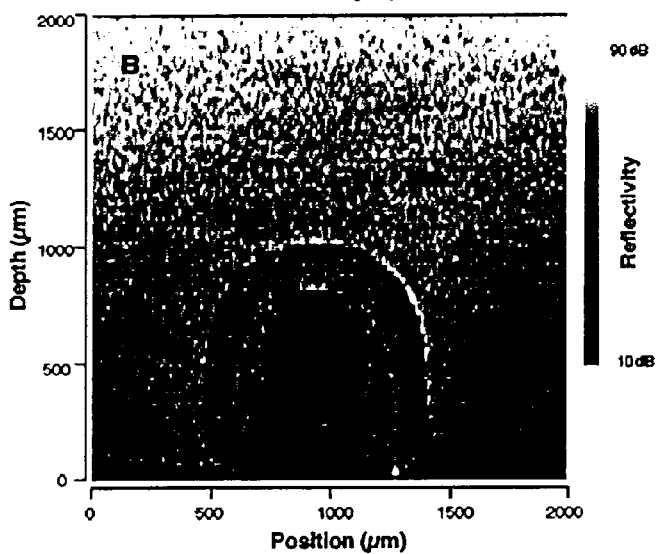
Figure 2C:
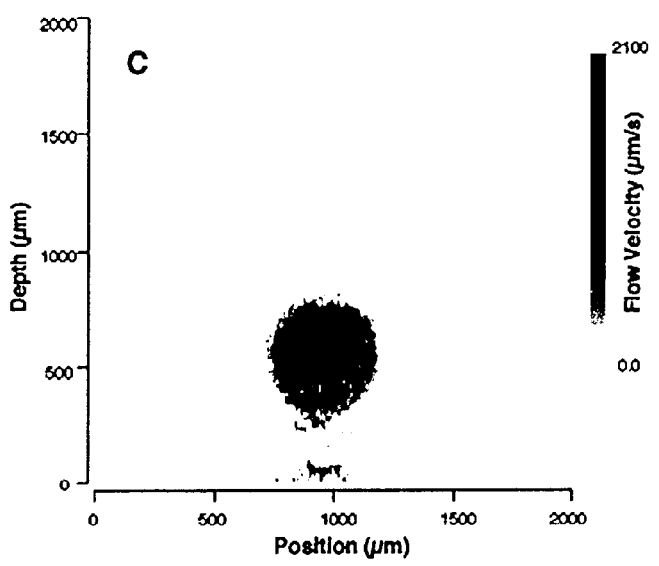

The tomographic images obtained from the system of FIG. 1 for the phantom models are shown at FIGS. 2a, b and c. FIG. 2a is the tomographic image of static polystyrene beads in conduit 28, FIG. 2b is the tomographic image of styrene beads flowing in conduit 28, and FIG. 2c is the velocity image of flowing beads in conduit 28. In FIGS. 2a and b the pixel intensity of the tomographic image shows reflectivity of the backscattered light in gray scale coded with a dark shading representing high reflectivity and light shading representing lower reflectivity. The vertical scale is depth within conduit 28 and bath 29 in microns while the horizontal axis is position of the pixel within conduit 28 and bath 29 in microns. In FIGS. 2a and b the shading changes from high reflectivity at the surface of bath 29 to low at the bottom of bath 29 indicating a strong attenuation of the probe beam by phantom bath 29. The dynamic range of the measured backscattered light in the tomographic structural image is approximately 100 dB.

The backscattered light from both the beads and conduit wall is evident in the image of FIG. 2a. The depth of the top surface of conduit 28 is 1 mm below the surface of phantom 29. FIG. 2b is the tomographic image recorded when the beads are flowing through conduit 28. All features of the image remain unchanged as compared to FIG. 2a except that the area within the circular conduit 28 appears darker. This effect is due to flowing beads that shift the interference fringe frequency away from the phase modulation frequency.

Figure 3:
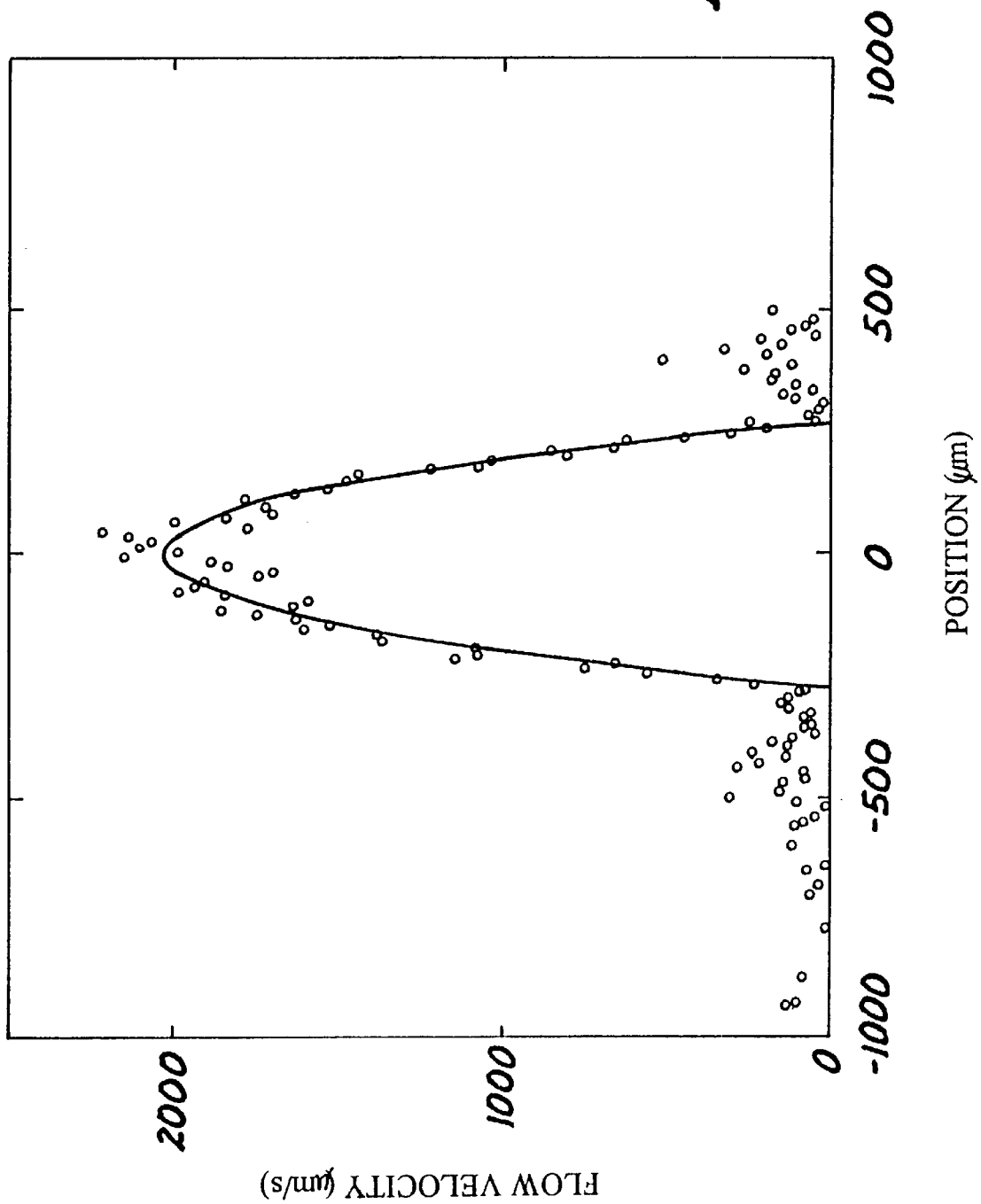
FIG. 3 is a graph of the flow velocity of the beads in the circular conduit of FIGS. 1 and 2a, 2b and 2c as a function of position from the center of the conduit where the data points are taken as discrete points while the solid curve is theoretical prediction assuming laminar flow.

FIG. 2c is a tomographic image of the velocity of the flowing beads where the features are gray scale coded with darker shading for high velocity in the range of 2100 microns per second to light shading for zero velocity. Static regions of conduit 28 and bath 29 appear white where velocity is near zero. Whereas the presence of beads moving at different velocities is evident in the tomograph of FIG. 2c, beads near the center of conduit 28 are observed to move faster than those near the conduit walls. For the flow velocity used in the experiment demonstrated in FIGS. 2a–c, laminar flow was used. The velocity profile of a laminar flow in circular conduit 28 has a parabolic form. A horizontal cross-section of the velocity profile at the center of the conduit is shown in FIG. 3 where velocity is graphed on the vertical axis in microns/second and radial position from the center of conduit 28 is graphed on the horizontal scale in microns. The data points are discretely indicated by open circles with a solid curve being a theoretical fit assuming laminar flow with a conduit of known diameter.

Figure 4:
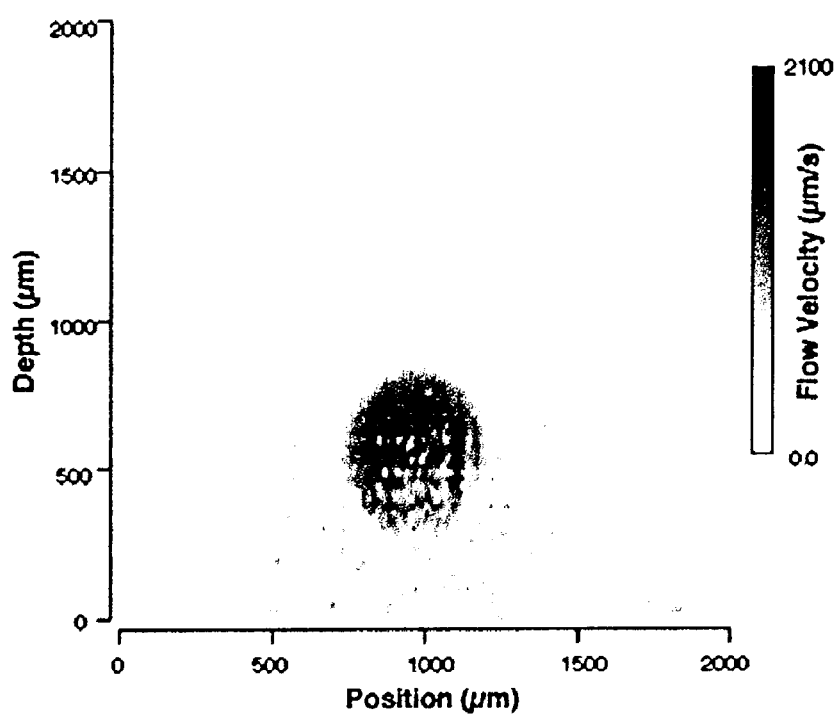
FIG. 4 is an optical Doppler tomographic image using the invention of flowing 1% intralipid and circular conduit as shown in FIG. 1 and FIGS. 2a, 2b and 2c submerged 1 mm below the surface in a scattering phantom of 1% intralipid solution.

In the second phantom model, a 1% intralipid fluid flowing through conduit 28 which is submerged in a highly scattering phantom bath 29 of 1% intralipid solution. A tomographic image of flow velocity is shown in FIG. 4 in which gray scale coding black is for high velocity at 2000 microns per second with white being zero velocity. Although scattering from the intralipid is high, $\mu_s = 23$ cm$^{-1}$ at a $\lambda_0$ of 850 nm and although conduit 28 as viewed from the top surface of phantom bath 29 is invisible to the unaided eye, the presence of beads flowing at different velocities is evident in the image of FIG. 4. These findings demonstrate that optical Doppler tomography is capable of detecting flow submerged in a highly scattering media similar to biological tissue.

Turn now and consider the ability of optical Doppler tomography to image in vivo blood flow. Two in vivo biological models are discussed below, namely the chick chorioallantoic membrane and rat skin. The chick chorioallantoic membrane is a well established model for studying microvasculature and has been used extensively to investigate the effects of vasoactive drugs, as well as optical and thermal processes in blood vessels. Because the chick chorioallantoic membrane microvasculature is located in a transparent matrix, simultaneous direct viewing and noninvasive imaging of the blood vessels are possible after the apex of the chick egg shell is removed. The effects of optical scattering in the biological tissue is demonstrated with the rat skin model.

In the chick chorioallantoic membrane model, blood flow in a vein is imaged to minimize the effect of pulsation. A structural tomographic image of chick chorioallantoic membrane blood flow shown in FIG. 5a and a velocity tomographic image shown in FIG. 5b were obtained simultaneously. The blood vessel wall, chorion membrane, and yolk sack membrane are evident in the structural image of FIG. 5a. In the tomographic velocity image of FIG. 5b, static regions where V=0 in the chick chorioallantoic membrane appear lightly colored while blood moving at different velocities is more darkly colored. Magnitude of blood flow velocity at the vessel center is maximum and decreases monotonically toward the peripheral wall of the blood vessel as shown in FIG. 5b.

A horizontal cross section of the velocity image near the vessel center is shown in FIG. 5c. The horizontal axis indicates position in the section in microns with the vertical sections showing velocity in microns/second. An excellent fit of the velocity profile to a parabolic function indicates that blood flow in the chick chorioallantoic membrane vein is a laminar.

To demonstrate the potential applications of optical Doppler tomography for in vivo blood flow monitoring after pharmacological intervention, the effect of a vasoactive drug on the chick chorioallantoic membrane vasculature is demonstrated below. Drops of the vasodilating drug, nitroglycerin, were applied to a chick chorioallantoic membrane artery. Arterial Doppler tomographic images before drug intervention as shown in the structural and velocity images of FIGS. 6a and 6b respectively and after drug intervention as shown in the structural and velocity images of FIGS. 6a' and b' respectively were recorded in the case of nitroglycerin. The arterial wall can clearly be identified and dilation of the vessel after nitroglycerin application is evident in the structural images by comparing FIGS. 6a and 6a'. Because of arterial blood flow pulsation, velocity images appear discontinuous in FIGS. 6b and 6b'. Linear or segmented features in arterial flow velocity images result from mixing of blood flow pulsation and the lateral scan frequencies. However, enlargement of the cross-sectional area of blood flow is also evident in the velocity images. These results demonstrate that optical Doppler tomography offers a noninvasive method for simultaneously probing changes in both blood flow dynamics and vessel structure.

In a Sprague-Dawley rat skin model, in vivo blood flow in both veins and arteries is imaged using optical Doppler technology as discussed below. Cross-sectional structural images are shown in FIG. 7a and velocity images in FIGS. 7b and c, which were obtained simultaneously. The presence of vessel like circular features can be observed in the structural image of FIG. 7a. Strong attenuation of light backscattered from locations deep in the skin indicates a high degree of optical scattering. Dynamic range of the measured backscattered light in the tomographic structural images is greater than 90 dB. Velocity images of blood flow moving in opposite directions, as determined by the sign of the Doppler frequency shifts are shown in FIGS. 7b and c. Venous blood flow is shown in FIG. 7b and arterial flow is shown in FIG. 7c. To demonstrate the versatility of optical Doppler tomography en face structural images as shown in FIG. 8a and velocity images shown in FIG. 8b of in vivo blood flow were recorded by scanning the sample beam focused at 200 microns below the skin surface. Blood flow in a branching vessel is clearly evident. These results demonstrate the generality by which optical Doppler tomography can be used for noninvasive imaging of in vivo blood flow velocity in highly scattering biological tissue.

The lateral and axial spatial resolutions of our optical Doppler tomographic system are limited by the beam spot size and spectral width of light source 10 to 5 and 13 microns respectively. Higher axial resolution can be achieved if a broader spectral source is used. Velocity resolution in the illustrated system is approximately 100 microns per second. This resolution depends on the data acquisition time at each pixel and the angle between the flow direction and sample beam. Velocity resolution can be improved if a smaller angle and/or a longer acquisition time is used. With a scanning speed of 800 microns per second, data acquisition time for optical Doppler tomographic images (1×1 mm$^2$) with 10 micron spatial resolution is approximately 3 minutes. Scanning speed is ultimately limited by the data acquisition time at each pixel, which effects the detection sensitivity of velocity resolution. For example, to resolve a 1 kHz Doppler shift, which corresponds to a velocity of 100 microns per second, if the angle between the probe beam and the flow direction is 70°, minimum data acquisition time in each pixel is approximately 1 millisecond. An optical Doppler tomographic image of 100×100 pixels could therefore be acquired in 10 seconds. Shorter acquisition times of 100 milliseconds are possible if alternative scanning techniques are implemented, for example if the time variation of interference fringe intensity of many pixels is recorded simultaneously as in the spectral scanning technique described below.

Photo receiver 36, amplifiers 42, and A-to-D converter 44 may be replaced in an alternative embodiment with measurement of the optical power spectra of the interference fringe intensity at multiple wavelengths with a digital optical spectrum analyzer. "Spectral scanning" is therefore defined herein as any measurement of the optical power spectra of the interference fringe intensity at multiple wavelengths.

Thus using spectral scanning the position and velocity of both moving and static tissue structures can be attained by measurement of the optical power spectrum of the interference fringe intensity. Spectral scanning provides for simultaneous measurement of the optical power spectrum of the interference fringe intensity at multiple wave lengths. Spectral scanning is fundamentally different from the prior art temporal or serial approach in that the interference between light backscattered from sample and reference mirror 32 is observed as a modulation of the optical power spectral density and occurs only for path length differences greater than the coherence length of source 10.

For purposes of illustration, the optical power spectral density, $S(v)$, corresponding to reflection from a single surface target with a reflectivity, $K_s$, in the sample arm with time dependent optical path length difference of $\Delta(t)$ is given by the formula:

$$S(v) = S_0(v)\left(|K_r|^2 + |K_s|^2 + 2K_rK_s\cos\left(\frac{4\pi v\Delta(t)}{c}\right)\right)$$

where $S_0(v)$ is the optical power spectral density of the partially coherent source at the optical frequency $v$, where $K_r$ is the amplitude reflectivity of the reference beam, and $K_s$ the amplitude reflectivity of the sample beam, which for simplicity is assumed to be frequency independent. When an object, the ith particle, measured is moving at a uniform velocity, $V_i$, so that $\Delta(t)$ is equal to $V_i t + \Delta_i$, then the optical power spectral density becomes:

$$S(v) = S_0(v)\left(|K_r|^2 + |K_s|^2 + 2K_rK_s\cos\left[\frac{4\pi v(\Delta_i + V_i t)}{c}\right]\right)$$

Here, $\Delta_i$ is the optical path length difference between light backscattered from object $O_i$ and the reference mirror at t=0. The algebraic expression for the optical spectral density, $S(v)$ is comprised of two terms corresponding to the interfering $S_I(v)$ and noninterfering $(S_r(v)+S_s(v))$ light given by the equations below:

$$S_r(v)+S_s(v)=S_0(v)(|K_r|^2+|K_s|^2)$$

Where $$\Gamma = \frac{c}{2\Delta_i} \text{ and } \Phi_i(t) = \frac{4\pi v t V_i}{c}.$$

The equations above include all of the information regarding position and velocity of an object which is contained in the interference term, $S_I(v)$. For measurement of blood flow in biological materials, red blood cell movement over the measured time, $t_m$, is much less than the optical path length difference $\Delta_i$ so that $V_i t_m$ is much less than $\Delta_i$. The position and velocity of a moving target may then be determined by respective measurement of the period, $\Gamma(\Delta_i)$, and the rate of phase change $$\frac{d\Phi_i}{dt}$$

of the modulation frequency with spectral period $\Gamma(\Delta_i)$, namely $$\frac{d\Phi_i}{dt} = \frac{4\pi v V_i}{c}$$

$$\Gamma(\Delta_i) = c/2\Delta_i$$

for each ith particle.

In biological materials, many tissue components contribute to spectral interference. If we only consider light incident on the sample that is singly backscattered, then the spectral interference term can be rewritten as, $$S_I(v) = 2S_0(v)K_r\sum_i K_i\cos\left[\frac{2\pi v}{\Gamma(\Delta_i)} + \Phi_i(t)\right]$$

Here, $\Delta_i$, is the optical path length difference of the ith tissue component contributing to backscatter, $\Phi_i$ is the phase change introduced by the movement of the ith tissue component. Thus, quantitative estimates of position, $\Delta_i$, and the velocity $V_i$ of each ith tissue component can be determined by computing the spectral periods $\Gamma(\Delta_i)$ and corresponding phase change rates $d\Phi_i/dt$ of the modulation frequencies with corresponding spectral periods $\Gamma(\Delta_i)$ of the interference spectral density. Thus by using an optical spectrum analyzer to look across the entire interference spectral density returned by the backscattered light through interferometer 8, the positions and corresponding velocities of moving targets in a single cross-section can be obtained without the need for an axial scan of the cross-section, thereby substantially reducing scan times.

Thus it may be possible with the benefit of spectral scanning to simply move scanning lens 30 the transverse width of the biological specimen or alternatively to provide a fiber optic scanning array feeding through interferometer 8 into an array detector coupled to a multiple channel optical spectrum analyzer, which provides for the interference spectral density at each longitudinal cross section corresponding to a separate fiber optic pickup position in the biological sample. In this way, through a single snapshot an entire biological sample can be simultaneously analyzed for particulate position and velocity through the entire volume or cross section of the biological target, thereby providing faster practical scan times.

Optical Doppler tomography has great potential for use in clinical management of patients who can benefit from microvasculature monitoring. The importance of blood flow monitoring is underscored by the high salvage rate of failing flaps and replants in surgical patients with expedient return to the operating room and exploration. Information provided by optical Doppler tomography could monitor and determine tissue profusion and viability before, during and after reconstructive procedures. Optical Doppler tomography also provides a means for determining the efficacy of pharmacological interventions for failing surgical flaps or replants, imaging microcirculation during sepsis, assessing burn depth, monitoring retinal and intraocular vascular flows in general and in particular in response to pharmacological manipulation, and investigating the mechanism of photodynamic therapy for cancer treatment. Because the data is obtained in the single scan, optical Doppler tomography permits tomographic imaging of both structural features and fluid flow velocity simultaneously. Given the noninvasive nature of the measurement, the exceptional spatial resolution, its simple hardware requirements, and relatively compact size, optical Doppler tomography is not only a promising technique for noninvasive in vivo imaging of blood flow velocity, but can also be applied to other areas where rapid noninvasive imaging of turbulent or laminar flow in optically scattering media is required.

For further examples, useful applications include but are not limited to: in situ three-dimensional tomographic structure and velocity profiles of blood perfusion in human skin at discrete spatial locations in either superficial or deep dermis; burn depth determinations to provide guidance for optimal depth of burn debridement prior to definitive closure; determination of tissue perfusion and viability immediately after injury; monitoring of tissue perfusion and viability after wound closure, replantation or transposition of either rotational or free skin flaps; potential evaluation of the vascular status of a buried muscle flap covered by a split thickness skin graft with perfusion in both the superficial and deeper flap components being monitored individually; determination of the extent of intestinal vascular insufficiency or infarction to conserve intestines by confining resection to those nonvascularized segments; determination of the presence or extent of adjacent post traumatic arterial or venous vascular injury by providing in situ tomograhic images and velocity profiles of blood flow; providing in situ tomographic images and velocity profiles of blood flow after reanastomosis of the artery or vein; provides distinction between arterial and venous occlusions; and provide monitoring of the efficacy of pharmacological interventions on microvascular blood flow.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, although the invention has been described in the context of biomedical applications, it can be applied in any situation involving a flow of turbid medium which includes many instances of material processing of paints, milk, pigmented fluids and other types of opaque liquids. Optical Doppler tomography could also be used to characterize dry particulate flow within conduits such as in a jet stream. Here, a significant advantage of the invention is that the flow could be characterized without disturbing the stream.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for tomographic imaging of a fluid flow in a highly scattering medium comprising:

providing a source of at least partially coherent radiation through an interferometer;

phase modulating said radiation in said interferometer at a modulation frequency;

continuously scanning a fluid flow sample with said source of at least partially coherent radiation through said interferometer, said fluid flow sample having a fluid flow therein and a structure in which said fluid flow is defined;

detecting interference fringes of said radiation backscattered from said sample into said interferometer; and data processing Doppler frequency changes of said detected backscattered interference fringes with respect to said modulation frequency at each pixel of a scanned image to continuously measure the interference fringe intensities to obtain time dependent power spectra for each pixel location in a data window in a continuous scan from which a tomographic image of the fluid flow in and the structure of said scanned fluid flow sample is formed.

2. The method of claim 1 where scanning said fluid flow sample with a source of at least partially coherent radiation comprises scanning said fluid flow sample with a source of low coherence radiation.

3. The method of claim 1 where scanning said fluid flow sample comprises scanning said fluid flow sample with said source of radiation through a fiberoptic Michelson interferometer.

4. The method of claim 1 wherein said interferometer has a reference beam and a sample beam and scanning said fluid flow sample with said source of radiation through said interferometer further comprises matching polarity and equalize optical path length differences of said reference and said sample beams to optimize fringe contrast in said interferometer.

5. A method for tomographic imaging of a fluid flow in a highly scattering medium comprising:

providing a source of at least partially coherent radiation through an interferometer;

phase modulating said radiation in said interferometer at a modulation frequency;

scanning a fluid flow sample with said source of at least partially coherent radiation through said interferometer;

detecting interference fringes of said radiation backscattered from said sample into said interferometer; and data processing Doppler frequency changes of said detected backscattered interference fringes with respect to said modulation frequency at each pixel of a scanned image to form a tomographic image of said scanned fluid flow sample, wherein said interferometer has a sample and a reference beam and wherein said reference beam is attenuated to reduce photon bunching noise and increase signal-to-noise ratio of interference fringes between said reference and a backscattered sample beam within said interferometer.

6. A method for tomographic imaging of a fluid flow in a highly scattering medium comprising:

provuding a source of at least partially coherent radiation through an interferometer;

phase modulating said radiation in said interferometer at a modulation frequency;

scanning a fluid flow sample with said source of at least partially coherent radiation through said interferometer;

detecting interference fringes of said radiation backscattered from said sample into said interferometer; and data processing Doppler frequency changes of said detected backscattered interference fringes with respect to said modulation frequency at each pixel of a scanned image to form a tomographic image of said scanned fluid flow sample, wherein said interferometer has a sample optical path and a reference optical path with a reference mirror disposed in said reference optical path, said radiation having a beam waist in said sample path which includes said fluid flow sample, said method further comprising dynamically maintaining a zero optical path length difference between said beam waist in said fluid flow sample and said reference mirror notwithstanding axial movement of said beam waist in said fluid flow sample by means of compensating axial movement of said reference mirror in said reference optical path as said fluid flow sample is scanned.

7. The method of claim 6 where scanning said fluid flow sample includes making a plurality of incremental axial scanning movements, and where maintaining said zero optical path length difference between said beam waist in said fluid flow sample and said reference mirror comprises compensating for each said incremental axial scanning movement with a corresponding axial movement in said reference mirror to maintain said optical path length changes in said sample and reference beams zero as said fluid flow sample is scanned.

8. An apparatus for optical Doppler tomographic imaging of fluid flow velocity in highly scattering medium comprising:

a source of at least partially coherent radiation;

an interferometer coupled to said source of radiation, said interferometer having a reference arm for a reference beam and a sample arm for a sample beam;

a modulator coupled to said interferometer for modulating optical path length difference in said reference and sample arms of said interferometer at a predetermined phase modulation frequency;

a scanner coupled to said interferometer for scanning a fluid flow sample with said sample beam of said interferometer;

a sensor coupled to said interferometer for detecting backscattered radiation received by said interferometer from said scanner to detect interference fringes within said interferometer; and a data processor coupled to said sensor for processing signals from said sensor corresponding to said interference fringes established by said backscattered radiation in said interferometer and for controlling said scanner to generate tomographic images, wherein said data processor generates a power spectrum of interference fringe intensity at each pixel defined within said scan, and wherein said data processor simultaneously generates a tomographic structural image and a tomographic flow velocity image from said power spectrum at each pixel in said image.

9. The apparatus of claim 8 further comprising a polarization element coupled to said interferometer to match polarity of said reference and sample beams to optimize fringe contrast and equalize optical path length difference.

10. An apparatus for optical Doppler tomographic imaging of fluid flow velocity in highly scattering medium comprising:

a source of at least partially coherent radiation;

an interferometer coupled to said source of radiation, said interferometer having a reference arm for a reference beam and a sample arm for a sample beam;

a modulator coupled to said interferometer for modulating optical path length difference in said reference and sample arms of said interferometer at a predetermined phase modulation frequency;

a scanner coupled to said interferometer for scanning a fluid flow sample with said sample beam of said interferometer;

a sensor coupled to said interferometer for detecting backscattered radiation received by said interferometer from said scanner to detect interference fringes within said interferometer; and a data processor coupled to said sensor for processing signals from said sensor corresponding to said interference fringes established by said backscattered radiation in said interferometer and for controlling said scanner to generate tomographic images, where said reference arm of said interferometer includes a reference mirror, and where said sample beam has a beam waist, said apparatus further comprising means for maintaining a zero optical path length difference between said sample and reference beams as said beam waist of said sample beam is axially moved in said sample by compensating axial movement of said reference mirror.

11. An apparatus for optical Doppler tomographic imaging of fluid flow velocity in highly scattering medium comprising:

a source of at least partially coherent radiation;

an interferometer coupled to said source of radiation, said interferometer having a reference arm for a reference beam and a sample arm for a sample beam;

a modulator coupled to said interferometer for modulating optical path length difference in said reference and sample arms of said interferometer at a predetermined phase modulation frequency;

a scanner coupled to said interferometer for scanning a fluid flow sample with said sample beam of said interferometer;

a sensor coupled to said interferometer for detecting backscattered radiation received by said interferometer from said scanner to detect interference fringes within said interferometer; and a data processor coupled to said sensor for processing signals from said sensor corresponding to said interference fringes established by said backscattered radiation in said interferometer and for controlling said scanner to generate tomographic images, wherein said data processor generates a power spectrum of interference fringe intensity at each pixel defined within said scan, and wherein said data processor simultaneously generates a tomographic structural image and a tomographic flow velocity image from said power spectrum at each pixel in said image.

12. A method for tomographic imaging of a fluid flow in a highly scattering medium comprising:

scanning a fluid flow sample with a source of at least partially coherent radiation through an interferometer to generate backscattered radiation in said interferometer;

phase modulating said radiation in said interferometer at a modulation frequency;

measuring spectral periods and phase change rates of modulation of an interference spectral density of said backscattered radiation in said interferometer; and generating a tomographic image of said scanned fluid flow sample from said spectral periods and phase change rates to simultaneously obtain positions and velocities of objects moving within said fluid flow sample.

13. The method of claim 12 where scanning said fluid flow sample comprises scanning said fluid flow sample with said source of radiation through a fiberoptic Michelson interferometer.

14. The method of claim 12 wherein said interferometer has a reference beam and a sample beam and scanning said fluid flow sample with said source of radiation through said interferometer further comprises matching polarity and equalizing optical path length differences of said reference and said sample beams to optimize fringe contrast in said interferometer.

15. The method of claim 12 wherein said interferometer has a sample and a reference beam and wherein said reference beam is attenuated to reduce photon bunching noise and increase signal-to-noise ratio of interference fringes between said reference and a backscattered sample beam within said interferometer.

16. The method of claim 12 wherein said interferometer has a sample and reference beam and wherein scanning said fluid flow sample with modulated radiation comprises modulating the optical path lengths of said radiation in said reference and sample beams of said interferometer.

17. The method of claim 12 wherein said modulation of said interference spectral density of said radiation is characterized by a plurality of frequencies and wherein measuring said frequencies and phase change rates of said modulation of said interference spectral density of said radiation in said interferometer is performed by measuring said spectral periods and phase change rates in an optical spectrum analyzer coupled to said interferometer to receive interference spectral density of said backscattered radiation in said interferometer.

18. The method of claim 12 wherein generating a tomographic image of said scanned fluid flow sample from said spectral periods and phase change rates to simultaneously obtain positiond and velocities of objects moving within said fluid flow sample, is obtained from said interference spectral density by obtaining a position of each object, $O_i$, in said fluid flow sample by measurement of a corresponding spectral period $\Gamma(\Delta_i)=C/2\Delta_i$, of a frequency in said interference spectral density, where c is the speed of light, and $\Delta_i$ is the path length difference of the $O_i$ object at t=0, where t is the time of measurement, and by measurement of a corresponding rate of phase change, $d\Phi_i/dt=4\pi \nu V_i/c$, of said spectral period in said inteference spectral density, where $V_i$ is the velocity of the $O_i$ object at t=0, $\nu$ is the frequency of said modulation, and c is the velocity of light.

19. An apparatus for optical Doppler tomographic imaging of fluid flow velocity in highly scattering medium comprising:

a source of at least partially coherent radiation;

an interferometer coupled to said source of radiation, said interferometer having a reference arm for a reference beam and a sample arm for a sample beam, and an output;

a modulator coupled to said interferometer for modulating optical path lengths in said reference and sample arms of said interferometer at a predetermined phase modulation frequency;

a probe coupled to said interferometer for exposing a fluid flow sample with said sample beam of said interferometer;

an optical spectrum analyzer coupled to said output of said interferometer for detecting backscattered radiation received by said interferometer from said probe to detect and analyze a plurality of modulated optical spectral interference densities produced by said interferometer; and a data processor coupled to said optical spectrum analyzer for processing signals from said probe for spectral scanning said fluid flow sample corresponding to said plurality of modulated optical spectral interference densities established by said backscattered radiation in said interferometer to generate tomographic images from said plurality of interference spectral densities.

20. The apparatus of claim 19 further comprising a polarization element coupled to said interferometer to match polarity and equalize optical path lengths of said reference and sample beams to optimize fringe contrast.

21. An apparatus for optical Doppler tomographic imaging of fluid flow velocity in highly scattering medium comprising:

a source of at least partially coherent radiation;

an interferometer coupled to said source of radiation, said interferometer having a reference arm for a reference beam and a sample arm for a sample beam, and an output;

a modulator coupled to said interferometer for modulating optical path lengths in said reference and sample arms of said interferometer at a predetermined phase modulation frequency;

a probe coupled to said interferometer for exposing a fluid flow sample with said sample beam of said interferometer;

an optical spectrum analyzer coupled to said output of said interferometer for detecting backscattered radiation received by said interferometer from said probe to detect and analyze modulated spectral interference densities produced by said interferometer; and a data processor coupled to said optical spectrum analyzer for processing signals from said probe corresponding to said interference spectral densities established by said backscattered radiation in said interferometer to generate tomographic images, wherein said optical spectrum analyzer measures spectral periods and phase change rates of said modulation of said interference spectral densities of said radiation in said interferometer.

22. The apparatus of claim 21 where said data processor generates a tomographic image of said fluid flow sample from said spectral periods and phase change rates to simultaneously obtain positions and velocities of objects moving within said fluid flow sample from said interference spectral densities by obtaining position of each object, $O_i$, in said fluid flow sample by measurement of a spectral period $\Gamma(\Delta_l)=c/2\Delta_l$, of a frequency in said interference spectral densities, where c is the speed of light, and $\Delta_l$ is the path length difference of the $O_i$ object at t=0, where t is the time of measurement, and by measurement of a corresponding rate of phase change, $d\Phi_j/dt=4\pi \nu V_i/c$, of said frequency in said interference spectral density, where $V_i$ is the velocity of the $O_i$ object at t=0, $\nu$ is the frequency of said modulation, and c is the speed of light.

* * * * *

UNITED STATES PATENT AND TRADEMARK OFFICE
CERTIFICATE OF CORRECTION

| | | |
|---|---|---|
| PATENT NO. | : 5,991,697 | Page 1 of 1 |
| APPLICATION NO. | : 08/775279 | |
| DATED | : November 23, 1999 | |
| INVENTOR(S) | : John S. Nelson, Thomas Edward Milner and Zhongping Chen | |

It is certified that error appears in the above-identified patent and that said Letters Patent is hereby corrected as shown below:

In column 1, line 5, after the title, please replace the statement of government support with the following corrected paragraph:

"This invention was made with government support under grants AR041638, AR042437, RR001192, and RR006988 awarded by the National Institute of Health, and grant DE-FG03-91ER61227 awarded by the Department of Energy. The government has certain rights in the invention."

Signed and Sealed this

Twenty-sixth Day of April, 2011

David J. Kappos
*Director of the United States Patent and Trademark Office*